United States Patent [19]

Yamamoto et al.

[11] Patent Number: 5,780,670
[45] Date of Patent: Jul. 14, 1998

[54] DTPA DERIVATIVES MODIFIED WITH NON-ESTER BOND AND A PROCESS FOR SYNTHESIZING THEM

[75] Inventors: Yoshinori Yamamoto, Sendai; Hisao Nemoto, Tokushima, both of Japan

[73] Assignee: Tohoku University, Sendai, Japan

[21] Appl. No.: 680,611

[22] Filed: Jul. 16, 1996

[30] Foreign Application Priority Data

Jul. 21, 1995 [JP] Japan ................... 7-185306

[51] Int. Cl.$^6$ ............................. C07C 229/00
[52] U.S. Cl. ......................... 560/169; 562/565
[58] Field of Search ................. 562/565; 560/169

[56] References Cited

U.S. PATENT DOCUMENTS 3,062,719  11/1962  Rubin ....................... 562/565
5,011,925  4/1991  Rajagopalan ............... 562/565

FOREIGN PATENT DOCUMENTS 0 603 03  6/1994  European Pat. Off. .

OTHER PUBLICATIONS

Chemical Reviews, vol. 93, No. 3, pp. 1137–1156, May 1, 1993, S. Jurisson, et al., "Coordination Compounds in Nuclear Medicine".

Progress in Neutron Capture Therapy for Cancer, pp. 231–233, 1992, A. D. Whittaker, et al., "Synthesis of $^{10}$B— and $^{157}$Gd–Labelled DNA Ligands for Neutron Capture Therapy".

Phys. Med. Biol., vol. 37, No. 1, pp. 155–162, 1992, Tetsuo Matsumoto, "Transport Calculations of Depth–Dose Distributions for Gadolinium Neutron Capture Therapy".

Tetrahedron Letters, vol. 37, No. 4, pp. 539–542, 1996, Hisao Nemoto, et al., "A New Synthetic Method of All Carboxylate–Free DTPA Derivatives and its Application to the Synthesis of Gd–Carborane Complex".

1995 International Chemical Congress of Pacific Basin Societies, Dec. 17–22, 1995, Dr. Jianping Cai, et al., "Synthesis of all Carboxylate–Free DTPA Derivatives via Palladium Catalyzed Carbon–Carbon Bond Formation Reaction".

*Primary Examiner*—Michael L. Shippen
*Attorney, Agent, or Firm*—Oblon, Spivak, McClelland, Maier & Neustadt, P.C.

[57] ABSTRACT

Provided are DTPA derivatives having five carbonyl groups, represented by the following formula (1). Further provided is a process for synthesizing a compound (1a) represented by the formula of a compound (1) in which $R_2$ is 2-alkenyl group ($R_4$). The process comprises the steps of performing esterification of DTPA, introducing an alkoxycarbonyl group and reacting with 2-alkenyl alkoxyformate in the presence of a palladium catalyst, thereby obtaining the compound (1a).

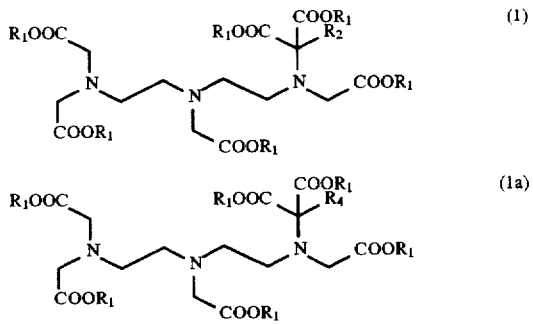

10 Claims, No Drawings

DTPA DERIVATIVES MODIFIED WITH NON-ESTER BOND AND A PROCESS FOR SYNTHESIZING THEM

BACKGROUND OF THE INVENTION

1. Field of the Invention

The present invention relates to diethylenetriamine pentaacetic acid derivatives modified with a non-ester bond, and more particularly to diethylenetriamine pentaacetic acid derivatives which can be clathration of a gadolinium ion and introduce a biological active site.

2. Description of the Related Art

Diethylenetriamine pentaacetic acid (hereinafter referred to as "DTPA") (4) is a compound widely used as a useful ligand for clathration of a metal ion (Wenzel, T. J., Bogyo, M. S. and Lebeau, E. L., J. Am. Chem. Soc., 1994, 116, 4858; Sieving, P. F., Watson, A. D., and Rocklage, S. M., "Gadolinium complexes for paramagnetically active protein conjugates," Bioconjugate Chem., 1990, 1, 65; Bailey, M. P., Rocks B. F., Riley C., "Lanthanide complexes for measurement of optical purity by NMR," Analyst, 1984, 109, 1449; Paik C. H., Sood, V. K., Le, N., Cioloca, L., Carrasquillo, J. A., Reynolds, J. C., Neumann, R. D., Rega, R. C., "Radioactive indidum complexes bearing antibodies," Nucl. Med. Biol., 1992, 19, 517.). Particularly, DTPA complex including a gadolinium ion (gadopentetic acid) (8) is used as a commercially available MRI contrast medium under a trade name "Magnebist" and used in the medical field (Wenzel, T. J., Bogyo, M. S. and Lebeau, E. L., J. Am. Chem. Soc., 1994, 116, 4858; Sieving, P. F., Watson, A. D., and Rocklage, S. M., "Gadolinium complexes for paramagnetically active protein conjugates," Bioconjugate Chem., 1990, 1, 65; Bailey, M. P., Rocks B. F., Riley C., "Lanthanide complexes for measurement of optical purity by NMR," Analyst, 1984, 109, 1449; Paik C. H., Sood, V. K., Le, N., Cioloca, L., Carrasquillo, J. A., Reynolds, J. C., Neumann, R. D., Rega, R. C., "Radioactive indidum complexes bearing antibodies," Nucl. Med. Biol., 1992, 19, 517.).

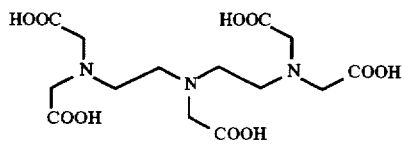

DTPA

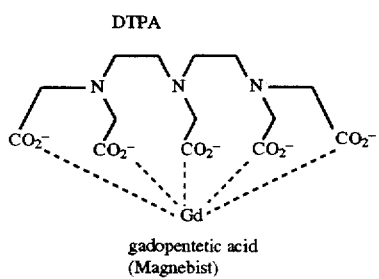

gadopentetic acid
(Magnebist)

As described above, DTPA including a metal ion such as a gadolinium ion is a complex which has attracted much attention in a variety of fields including the medical field.

On the other hand, a method for using DTPA complex as a medicament by modification of introducing a biological active site into DTPA has been studied (Bailey M. P., Rocks B. F., Riley C., "Lanthanide complexes for measurement of optical purity by NMR," Analyst, 1984, 109, 1449).

Hitherto, the modification of DTPA has been performed by binding a biological active site to one of five carbonyl groups of DTPA by an ester bond or an amide bond as shown in the following formulas (Wenzel, T. J., Bogyo, M. S. and Lebeau, E. L., J. Am. Chem. Soc., 1994, 116, 4858; Sieving, P. F., Watson, A. D., and Rocklage, S. M., "Gadolinium complexes for paramagnetically active protein conjugates," Bioconjugate Chem., 1990, 1, 65; Bailey, M. P., Rocks B. F., Riley C., "Lanthanide complexes for measurement of optical purity by NMR," Analyst, 1984, 109, 1449; Paik C. H., Sood, V. K., Le, N., Cioloca, L., Carrasquillo, J. A., Reynolds, J. C., Neumann, R. D., Rega, R. C., "Radioactive indidum complexes bearing antibodies," Nucl. Med. Biol., 1992, 19, 517.).

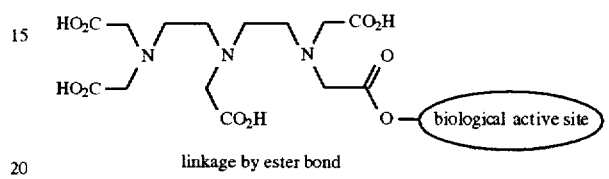

linkage by ester bond

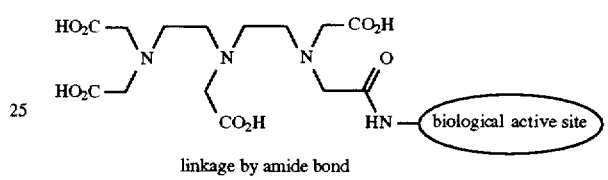

linkage by amide bond

In such a modification method of DTPA, one of five carboxyl groups of DTPA is converted into an ester or an amide. Consequently, the carboxyl groups capable of coordinating to a metal ion is reduced in number to four. Such reduction of number of the carboxyl groups may result in a lowering DTPA coordination ability, and lead to a problem in that a metal ion is liberated in vivo (Deshpanda S. V., Subramanian, R., McCall, M. J., DeNardo, G. L., Meares, C. F., J. Nuclear Med., 1990, 31, 218; Meares, C. F., McCall, M. J., Reardan, D. T., Goodwin, D. A., Diamanti, C. I., Mctigue, M., Anal. Biochem., 1984, 142, 68; Meares, C. F., Goodwin, D. A., J. Protein Chem., 1984, 3, 215.).

The present invention has been made in view of the aforementioned problem and is intended to provide derivatives of DTPA introduced an organic group by use of none of the five carboxyl groups.

The present invention is also directed to a process for synthesizing the DTPA derivatives.

SUMMARY OF THE INVENTION

An object of the present invention is to provide a diethylenetriamine pentaacetic acid derivative (1) represented by the following formula:

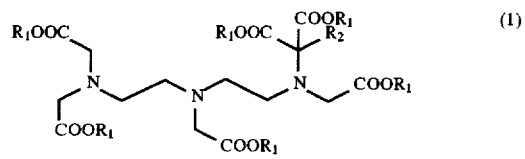

wherein $R_1$ is hydrogen or lower alkyl group, $R_2$ is hydrogen, alkyl group or alkenyl group.

Another object of the present invention is to provide a diethylenetriamine pentaacetic acid derivative (2) represented by the following formula:

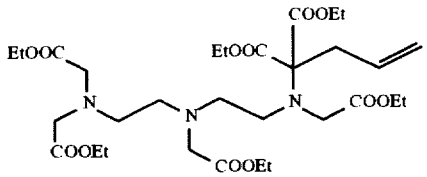

Still another object of the present invention is to provide a diethylenetriamine pentaacetic acid derivative (3) represented by the following formula.

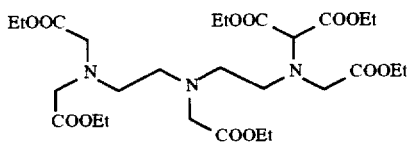

A further object of the present invention is to provide a process for synthesizing a diethylenetriamine pentaacetic acid derivative (1a) represented by the following formula:

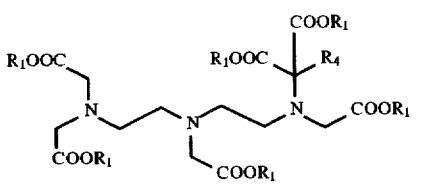

wherein $R_1$ is a lower alkyl group; $R_4$ is a 2-alkenyl group.

The process of the present invention comprises the steps of:

(a) obtaining a pentaester derivative (5) by reacting diethylenetriamine pentaacetic acid (4) with an alcohol in the presence of acid.

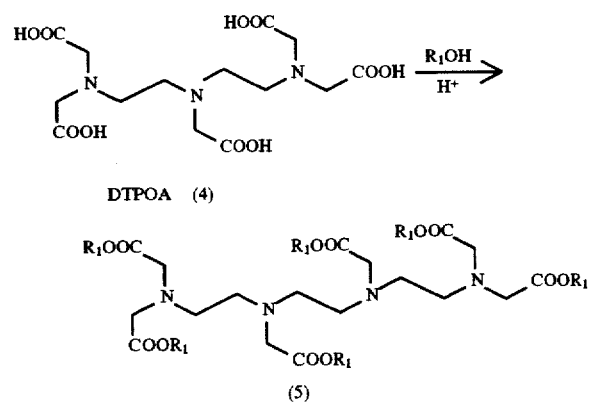

wherein $R_1$ is as defined above formula (1a);

(b) obtaining a compound (6) by treating the pentaester derivative (5) obtained in the aforementioned step (a) with base, followed by reacting with chloroformic acid ester.

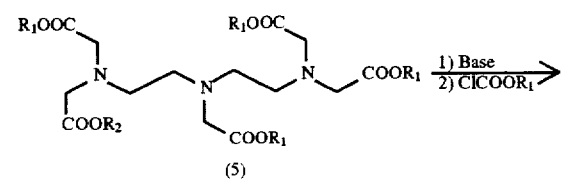

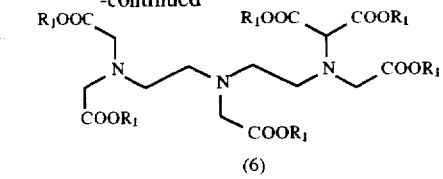

wherein $R_1$ is as defined above formula (1a); and (c) reacting the compound (6) obtained in the aforementioned step (b) with alkenyl alkoxyformate (7) in the presence of a palladium catalyst and an organic phosphine;

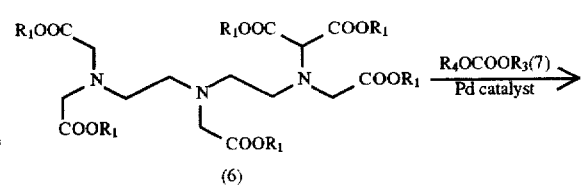

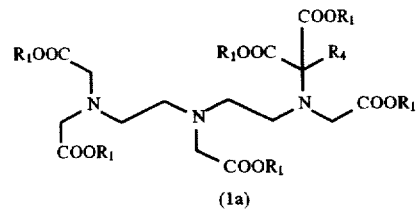

wherein $R_1$ and $R_4$ are as defined above formula (1a); $R_3$ is a lower alkyl group.

The compound (1) of the present invention can be covalently bonded to a biological active site with clue to a double bond of 2-alkenyl group or lengthened a carbon chain of DTPA by C—C bond, with the five carboxyl groups of DTPA remaining unchanged.

Particularly in the compound (2) of the present invention, a biological active site, for example, is covalently bonded to the compound (2) by reaction with a double bond of an allyl group. Thereafter, the compound introduced the biological active site is hydrolyzed and by the hydrolysis treatment, one carboxyl group on the carbon atom with attached the allyl group is simultaneously decarboxylated to give a compound introduced the biological active site or lengthened the carbon chain of DTPA by C—C bond, with the five carboxyl groups of DTPA remaining unchanged. The compound, if used for forming a complex with a metal ion, can coordinate to the metal ion more tightly, by virtue of the presence of five free carbonyl groups, than a DTPA derivative having a biological active site introduced by ester bond or amide bond.

The compound (3) of the present invention is an important intermediate for synthesizing the aforementioned compound (1) or (2).

Furthermore, the present invention provides a general process for synthesizing a particularly important compound (1a) of the aforementioned compounds (1). The process is a usually-used one performed using easily available compounds.

DETAILED DESCRIPTION OF THE PREFERRED EMBODIMENT

The compound of the present invention (1) is characterized by having an alkyloxycarbonyl group and organic group $R_2$ which are bound to one of two alkyloxycarbonylmethyl group on N atom at the end of DTPA. Because of such characteristics, the compound (1) has a specific feature in that an organic group can be introduced by non-ester bond, with five carboxylic groups of DTPA remaining unchanged.

$R_1$ of the compound (1) used herein represents a hydrogen or a straight or branched lower alkyl group having 1 to 6 carbon atoms. The lower alkyl group of $R_1$ include methyl, ethyl, n-propyl, isopropyl, n-butyl, sec-butyl, tert-butyl, n-pentyl, n-hexyl and the like. However, $R_1$ is not limited to these examples. A preferable example of $R_1$ is hydrogen or ethyl.

$R_2$ represents hydrogen or 2-alkenyl group. The 2-alkenyl group is a straight or branched alkenyl group having 2 to 6 carbon atoms. Specific Examples of the 2-alkenyl group include an allyl group, 2-butenyl group, 2-pentenyl group, 2-hexyl group and the like. A preferable example of $R_2$ is an allyl group.

The compound (1) of the present invention, unlike the DTPA modified in a conventional manner, is capable of tight coordination to a metal ion since it possesses five carboxyl groups.

In the case of the compound (2) in which $R_1$ of the compound (1) is an ethyl group and $R_2$ is an allyl group, various organic groups can be introduced into the compound at a position of a double bond of the allyl group by a known method. In addition, ester group, $R_1$ is hydrolyzed and by the hydrolysis treatment, one carboxyl group on t13he carbon atom with attached the allyl group is simultaneously decarboxylated to give a DTPA derivative introduced an organic group with the five carboxyl groups of DTPA remaining unchanged. Likewise, the compound of the present invention (1) may be an important intermediate developing into various DTPA derivatives lengthened a C—C bond with the five carboxylic acid groups remaining unchanged.

On the other hand, the compound (3) represented by the formula (1) in which $R_1$ is ethyl and $R_2$ is hydrogen, is an important intermediate for synthesizing the compound (1) and may be a useful chelating agent if deprotected.

Hereinbelow, the process for synthesizing the compound (1a) of the present invention will be explained in accordance with the steps.

The compound (1a) is a compound represented by the aforementioned formula (1) in which $R_1$ is a same lower alkyl group as $R_1$, and $R_4$ are the same as $R_2$ group, namely, a 2-alkenyl group, in the above formula (1).

In the process of the present invention, $R_3$ is a straight or branched lower alkyl group having 1 to 6 carbon atoms. Specific Examples of $R_3$ include methyl, ethyl, n-propyl, isopropyl, n-butyl, sec-butyl, tert-butyl, n-pentyl, n-hexyl and the like. However, $R_3$ is not restricted to these examples. Preferable example of $R_3$ is methyl.

$R_4$ is a straight or branched 2-alkenyl group having 2 to 6 carbon atoms. Specific examples of $R_4$ include an allyl group, 2-butenyl group, 2-pentenyl group, 2-hexyl group and the like. Preferable example of $R_4$ is an allyl group.

In the step (a), a carboxyl group of DTPA is protected as an ester. In the esterification, a conventional esterification reaction may be used. For example, the esterification is performed in the presence of acid. To be more specific, DTPA is treated in an alcohol as a solvent in the presence of a strong acid such as concentrated sulfuric acid, concentrated hydrochloric acid, or p-toluenesulfonic acid. The alcohol used is not particularly restricted. A lower alcohol is preferably used, more preferably methanol, ethanol, propanol and the like, and most preferably ethanol. Since the alcohol used also acts as a solvent, other solvent is not required. However, if necessary, a solvent may be used. In any case, an alcohol must be used in excess. The preferred alcohol to be used is an absolute alcohol.

A reaction temperature may preferably be at an appropriate temperature ranging from 50° C. to a reflux temperature of the alcohol employed. A preferred reaction time may be from 1 to 24 hours.

After completion of the reaction, the resultant reaction solution is made basic with an aqueous alkaline solution such as an aqueous sodium hydroxide. The product obtained is separated and purified by appropriate manner such as silica gel column chromatography or recrystallization.

In the step (b), a compound (6) is obtained from the pentaester derivative (5) prepared in the above step (a) by introducing an alkoxycarbonyl group.

In this step, the compound (5) is treated with base such as potassium bis(trimethylsilyl)amide (KBMSA), lithium diisopropylamide, or sodium bis(trimethylsilyl)amide and then treated with an alkyl chloroformate wherein the alkyl group is the same lower alkyl group as defined above $R_1$. Preferable examples of the alkyl chloroformate include methyl chloroformate, ethyl chloroformate, propyl chloroformate, and the like. The most preferable example is ethyl chloroformate.

The alkyl chloroformate is used in an amount of 2 to 4 equivalents based on that of the compound (5), and preferably used in an amount of 2.5 to 3 equivalents. The reaction is performed by use of an ethereal solvent such as diethyl ether or THF. The reaction may be carried out at a temperature of −60° to −80° C., preferably at −78° C. The treatment with base is performed for 20 minutes to 2 hours. The treatment with an alkyl chloroformate is carried out for 20 minutes to one hour. The compound (6) can be separated and purified by appropriate manner such as silica gel column chromatography or recrystallization.

In the step (c), an $R_4$ group is introduced into the compound (6) obtained in the above step (b). In this step, the alkoxyformate (7) is reacted with the compound (6) in the presence of a palladium catalyst such as palladium.2 (benzylidene acetone) [pd(dba)$_2$], and 1,2-bis (diphenylphosphino)ethane (dppe).

The alkoxyformate (7) is not particularly restricted as long as it can introduce an $R_4$ group, namely, 2-alkenyl group, into the compound (6). Preferable examples of the alkoxyformate (7) include allyl alkoxyformate, 2-butenyl alkoxyformate, 2-pentenyl alkoxyformate, 2-hexyl alkoxyformate and the like. The alkyl group, $R_3$ in the alkoxyformate is as defined above. The reaction is performed in an ethereal solvent such as THF. The palladium catalyst employed is used in an amount of 5 to 15 mol %, preferably 10 mol % based on the amount of the compound (6). The alkoxyformate (7) is used in an amount of 2 to 4 equivalents, preferably 2.5 to 3 equivalents based on the amount of the compound (6). The reaction temperature is from 50° to 150° C., preferably from 50° to 100° C., and more preferably from 50° to 80° C. The reaction time is 1 to 20 hours, preferably, 1 to 10 hours, and more preferably, 1 to 5 hours.

In the present invention, as a catalyst, Pd$_2$(dba)$_3$.CHCl$_3$ may be used in place of the aforementioned Pd(dba)$_2$. In place of dppe, triphenylphosphine, trimethylol propanephosphite and the like may be used. However, dppe is the most preferable.

The compound (1a) obtained can be separated and purified by appropriate manner such as silica gel column chromatography or recrystallization.

In this step, owing to the use of the Pd catalyst, a 2-alkenyl group can be selectively introduced into the compound (6).

From the foregoing, it is clear that the compound (1a) of the present invention can be synthesized through the aforementioned steps.

The obtained compound (1a) may be converted into a compound (9) which have five free carboxyl groups by hydrolysis and simultaneous decarboxylation of one carboxyl group on the carbon atom with attached $R_4$ group by the hydrolysis treatment.

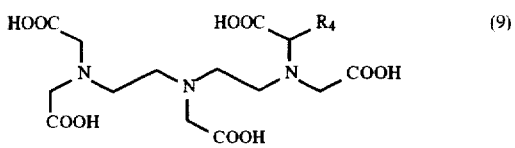

The hydrolysis of ester may be performed by a conventional deesterification reaction. To be more specific, the compound (1) is treated, for example, in an aqueous alcohol solution of lithium hydroxide and then acidified with a diluted acid such as 1N hydrochloric acid to afford the compound (9). This reaction is performed at a temperature of 0° to 50° C., preferably 10° to 25° C. The reaction time is 1 to 40 hours, preferably 1 to 20 hours, more preferably, 1 to 10 hours. The obtained compound (9) can be separated and purified by appropriate manner such as silica gel column chromatography or recrystallization.

Hereinbelow, the present invention will be described in detail by way of Example, which should not be construed as limiting the scope of the present invention.

In Example below, we will explain the present invention with reference to the case of the compound (2) in which $R_1$ is an ethyl group, and $R_4$ is an allyl group in compound (1a). Various alternations and modifications may be made by one skilled in the art, but such alternations and modifications will be included in the scope of the present invention.

EXAMPLE 1

Step (a): Synthesis of pentaethyl ester of DTPA (5a)

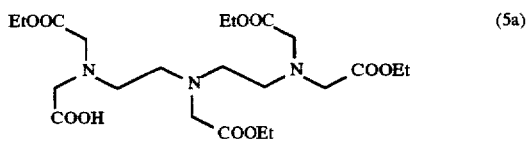

Diethylenetriamine pentaacetic acid (DTPA) (25 g, 63.5 mmol) and concentrated sulfuric acid (10 ml, 180 mmol) were dissolved in 500 ml of absolute ethanol. The mixture was refluxed for 20 hours. The reaction mixture was concentrated and the resulting residue was diluted with methylene chloride. Ten percent aqueous solution of NaOH was added to the reaction solution at 0° C. to make the solution alkaline. An organic layer was separated, dried over anhydrous MgSO$_4$ and filtrated. The filtrate was concentrated, and then purified by silica gel column chromatography with hexane:ethyl acetate=2:3 as an eluent to give a pure ethyl ester (5a) (26.88 g, 50.4 mmol, 78.3%).

IR (Film): 2979s, 1735s, 1029s, 728m cm$^{-1}$.

$^1$H-NMR (CDCl$_3$): δ (ppm) 4.21–4.1 (m, 10H), 3.57 (s, 8H), 3.49 (s, 2H), 2.9–2.75 (m, 8H), 1.27 (t, J=7.5 Hz, 12H), 1.26 (t, J=7.5 Hz, 3H).

$^{13}$C-NMR (CDCl$_3$): δ (ppm) 171.5(q), 171.2(q), 60.3(d), 60.1(d), 55.2(d), 52.7(d), 52.2(d), 14.2(s).

Anal. Cal. for C$_{24}$H$_{43}$N$_3$O$_{12}$: C 54.02, H 8.12, N 7.87; found C 53.79, H 7.88, N 7.72.

Step (b): Synthesis of compound (3)

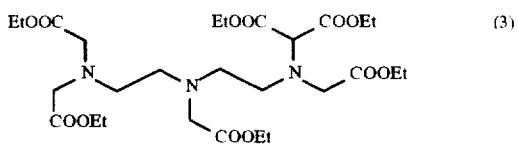

Potassium bis(trimethylsilyl)amide (0.5M toluene solution, 15 ml, 7.5 mmol) and THF were added to 100 ml flask cooled to −78° C. under a nitrogen atmosphere. To this solution, a compound (5a) obtained in the above step (a) (2 g, 3.75 mmol) in 30 ml of THF was slowly added dropwise over a period of 12 minutes. After the reaction mixture was stirred for 70 minutes at −78° C., ethyl chloroformate (1.22 g, 11.25 mmol) in 30 ml of THF was added dropwise over a period of 20 minutes. The resulting mixture was further stirred for 50 minutes. The reaction was quenched by adding aqueous 2N NH$_4$Cl solution and ether which were previously cooled. The resultant reaction mixture was extracted with ether, dried over MgSO$_4$, and filtrated. The filtrate was concentrated and the resulting residue was purified by silica gel column chromatography with benzene:ethyl acetate=2:1 as an eluent to give a pure compound (3) (1.2 g, 1.98 mmol, 52.8%).

IR (Film): 2980s, 1728s, 1034s, 728m cm$^{-1}$.

$^1$H-NMR (CDCl$_3$): δ (ppm) 4.48 (s, 1H), 4.27–4.06 (m, 12H), 3.67 (s, 2H), 3.56 (s, 4H), 3.48 (s, 2H), 2.97–2.73 (m, 8H), 1.33–1.2 (m, 18H).

$^{13}$C-NMR (CDCl$_3$): δ (ppm) 171.6(q), 171.3(q), 168.4(d), 168(q), 67.5(t), 61.4(d), 61.5(d), 60.4(d), 60.2(d), 55.2(d), 55.1(d), 53.5(d), 53.2(d), 52.7(d), 52.3(d), 51.5(d), 14.5(s).

Anal. Cal. for C$_{27}$H$_{47}$N$_3$O$_{12}$: C 53.54, H 7.82, N 6.94; found C 53.36, H 7.51, N 6.78.

Step (C): Synthesis of compound (2)

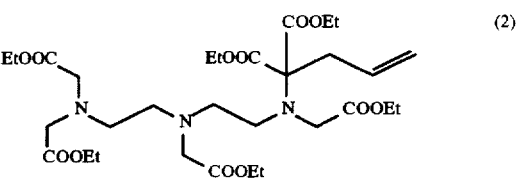

Allyl ethoxyformate (7a) (259 mg, 2.23 mmol), Pd(dba)$_2$ (42.5 mg, 0.074 mmol), dppe (59 mg, 0.148 mmol) and the compound (3) (450 mg, 0.74 mmol) obtained in the above step (b) were dissolved in 5 ml of THF. The reaction mixture was refluxed for 3 hours. After removal of the solvent, the residue was purified by silica gel column chromatography with benzene:ethyl acetate=2:1 as an eluent to give a pure compound (2) (383.8 mg, 0.59 mmol, 80.3%).

IR (Film): 3075w, 2982s, 1730s, 1639m, 1446s, 725m cm$^{-1}$.

$^1$H-NMR (CDCl$_3$): δ (ppm) 5.95–5.78 (m, 1H), 5.15–5.01 (m, 2H), 4.25–4.07 (m, 12H), 3.57 (s, 2H), 3.55 (s, 4H), 3.45 (s, 2H), 2.97–2.71 (m, 8H), 1.27 (t, J=7 Hz, 18H).

$^{13}$C-NMR (CDCl$_3$): δ (ppm) 171.8(q), 171.5(q), 171.3(q), 169.6(q), 132.8(t), 118(d), 75(q), 61.3(d), 60.4(d), 60.3(d), 60.2(d), 55.5(d), 55.3(d), 54(d), 52.9(d), 52.8(d), 52.4(d), 50.4(d), 38.9(d), 14.2(s).

Anal. Cal. for C$_{30}$H$_{51}$N$_3$O$_{12}$: C 55.8, H 7.96, N 6.51; found C 55.73, H 7.66, N 6.49.

What is claimed is:

1. A diethylenetriamine pentaacetic acid derivative represented by the following formula (1):

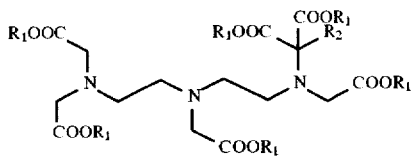

wherein $R_1$ is a hydrogen or a lower alkyl group, $R_2$ is hydrogen, or 2-alkenyl group.

2. A diethylenetriamine pentaacetic acid derivative represented by the following formula (2):

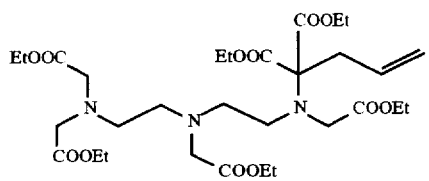

3. A diethylenetriamine pentaacetic acid derivative represented by the following formula (3):

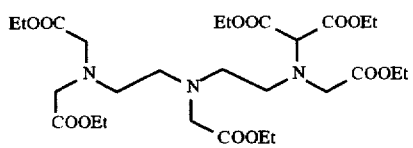

4. A process for synthesizing a diethylenetriamine pentaacetic acid derivative represented by the following formula (1a)

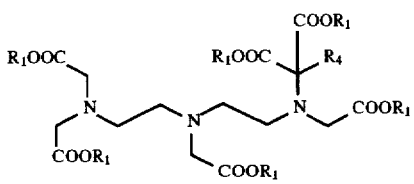

wherein $R_1$ is a lower alkyl group; $R_4$ is a 2-alkenyl group, which comprises the steps of:

(a) obtaining a pentaester derivative (5) by reacting diethylenetriamine pentaacetic acid (4) with an alcohol in the presence of acid,

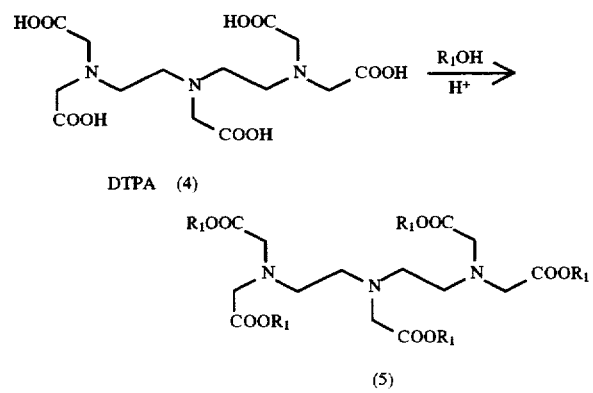

wherein $R_1$ is as defined above compound (1a);

(b) obtaining a compound (6) by treating the pentaester derivative (5) obtained in said step (a) with base, followed by reacting with alkyl chloroformate,

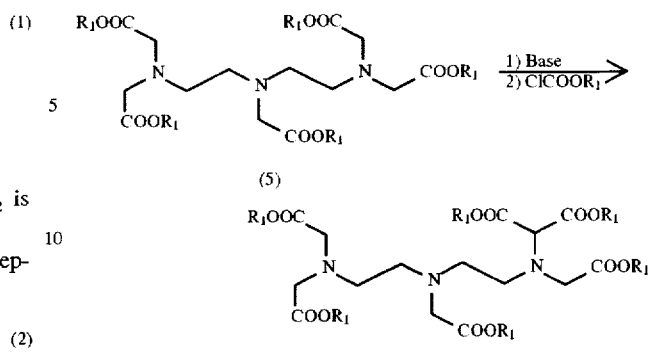

wherein $R_1$ is as defined above compound (1a); and (c) reacting the compound (6) obtained in the said step (b) with alkoxyformate (7) in the presence of a palladium catalyst and an organic phosphine;

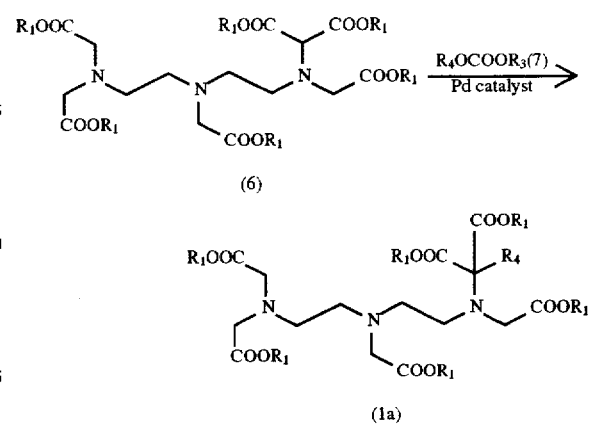

wherein $R_1$ and $R_4$ are as defined above compound (1a); $R_3$ is a lower alkyl group.

5. The compound according to claim 1, wherein said $R_1$ is selected from the group consisting of methyl, ethyl, n-propyl, isopropyl, n-butyl, sec-butyl, tert-butyl, n-pentyl and n-hexyl and said $R_2$ is selected from the group consisting of an allyl group, 2-butenyl group, 2-pentenyl group and 2-hexyl group.

6. The process according to claim 4, wherein, in said step (a), said alcohol is selected from the group consisting of methanol, ethanol and propanol, and said acid is selected from the group consisting of concentrated sulfuric acid, concentrated hydrochloric acid and toluenesulfonic acid.

7. The process according to claim 4, wherein, in said step (b), said base is selected from the group consisting of potassium bis(trimethylsilyl)amide (KBMSA), lithium diisopropylamide and sodium bis(trimethylsilyl)amide and said alkyl chloroformate is selected from the group consisting of methyl chloroformate, ethyl chloroformate and propyl chloroformate.

8. The process according to claim 4, wherein said organic phosphine in step (c) is selected from the group consisting of 1,2-bis(diphenylphosphino)ethane (dppe), triphenylphosphine, and trimethylol propanephosphite.

9. The process according to claim 4, wherein said alkoxyformate in said step (c) is selected from the group consisting of allyl alkoxyformate, 2-butenyl alkoxyformate, 2-pentenyl alkoxyformate and 2-hexyl alkoxyformate.

10. The process according to claim 4, wherein said palladium catalyst in said step (c) is selected from the group consisting of palladium.2(benzylideneacetone) |pd(dba)$_2$| and Pd$_2$(dba)$_3$.CHCl$_3$.

* * * * *